United States Patent [19]
LeVaughn et al.

[11] Patent Number: 5,868,772
[45] Date of Patent: Feb. 9, 1999

[54] BLOOD SAMPLING DEVICE WITH ANTI-TWIST LANCET HOLDER

[75] Inventors: Richard W. LeVaughn, McDonough, Ga.; Joseph E. Ruggiero, Goshen, Ind.; William C. Taylor, Rex, Ga.

[73] Assignee: Bayer Corporation, Elkhart, Ind.

[21] Appl. No.: 903,702

[22] Filed: Jul. 31, 1997

[51] Int. Cl.$^6$ ................................................. A61B 17/14
[52] U.S. Cl. ............................................ 606/181; 600/573
[58] Field of Search .................................. 600/573, 576, 600/583; 606/181, 182

[56] References Cited

U.S. PATENT DOCUMENTS

| | | | |
|---|---|---|---|
| 4,535,769 | 8/1985 | Burns | 606/182 |
| 4,895,147 | 1/1990 | Bodicky et al. | 606/182 |
| 5,100,427 | 3/1992 | Crossman et al. | 606/182 |
| 5,487,748 | 1/1996 | Marshall et al. | 606/182 |
| 5,554,166 | 9/1996 | Lange et al. | 606/182 |
| 5,611,809 | 3/1997 | Marshall et al. | 606/182 |
| 5,628,764 | 5/1997 | Schraga | 606/182 |
| 5,741,288 | 4/1998 | Rife | 606/181 |

*Primary Examiner*—Michael Peffley
*Assistant Examiner*—Charles Marmor, II
*Attorney, Agent, or Firm*—Roger N. Coe

[57] ABSTRACT

A blood sampling device is provided with a housing, a lancet assembly, a lancet holder which is movable in a lancing direction between a cocked position and a puncture position, and an actuator mechanism disposed in the housing for causing the lancet holder to move from the cocked position to the puncture position. The lancet assembly has a lancet with a sharp tip, a lancet body having at least two angularly spaced ribs which extend outwardly from a central portion of the lancet body, and a protective cap covering the sharp tip of the lancet, the protective cap being attached to the lancet body so that the protective cap is twistably removable from the lancet body. The lancet holder has an aperture formed therein, the aperture having a cylindrical shape and being substantially unobstructed so that the lancet body may be inserted into the aperture in any angular orientation relative to the lancet holder, and the blood sampling device includes a mechanism for preventing significant rotational movement of the lancet body relative to the lancet holder when the lancet body is disposed in the aperture formed in the lancet holder and when the protective cap is subject to an angular force sufficient to twist the protective cap off of the lancet body.

13 Claims, 2 Drawing Sheets

5,868,772

BLOOD SAMPLING DEVICE WITH ANTI-TWIST LANCET HOLDER

BACKGROUND OF THE INVENTION

The present invention relates to a blood sampling device that incorporates a lancet assembly for piercing the skin, and more particularly to a blood sampling device having a particular type of lancet holder for holding the lancet assembly.

A conventional blood sampling device has a lancet assembly in the form of a generally cylindrical plastic body in which a needle-like lancet is disposed. A portion of the plastic body has a number of outwardly extending ribs disposed thereon. A conventional lancet assembly is shown, for example, in FIG. 6 of U.S. Pat. No. 4,976,724 to Nieto, et al. The lancet assembly is held within a generally cup-shaped lancet holder by an interference fit. The lancet holder is typically disposed within a housing along with an actuator mechanism for moving the lancet holder between a cocked position, a puncture position, and a resting position intermediate the cocked and puncture positions.

A conventional lancet assembly also includes a plastic protective cap that covers the sharp tip of the lancet to prevent inadvertent skin puncture prior to use of the blood sampling device. When a blood sample is to be taken, the lancet assembly is forced into the cylindrical opening formed in the cup-shaped lancet holder, and the protective cap is twisted off the lancet assembly so that the tip of the lancet is exposed. To prevent the lancet assembly from turning within the lancet holder when the protective cap is twisted off (the interference fit is typically not strong enough to prevent such turning), the interior of a conventional, industry standard lancet holder is provided with a plurality of angularly spaced ribs which prevent rotation of the lancet assembly by making contact with the outwardly extending ridges of the lancet body. Although such ribs are useful in preventing unintended rotation of the lancet assembly relative to the lancet holder when the protective cap is twisted off, they may hinder the insertion of the lancet assembly into the lancet holder if the lancet assembly is not properly oriented relative to the lancet holder. This may cause frustration to the user of the blood sampling device and/or improper seating of the lancet assembly within the lancet holder.

U.S. Pat. No. 4,442,836 to Meinecke, et al. discloses a blood lancet device having a lancet holder of the type described above which is adapted to be inserted into a lancet holder having a hexahedral-shaped aperture with a square cross-section, as shown in FIG. 6 of the patent. The Nieto, et al. patent referred to above discloses a blood sampling device in which a lancet assembly having a protective cap is inserted into a collar-shaped lancet-holding mechanism having a tubular chamber, with an interference fit between the lancet assembly and the lancet holding mechanism.

SUMMARY OF THE INVENTION

The invention is directed to a blood sampling device having a housing, a lancet assembly, a lancet holder which is movable in a lancing direction between a cocked position and a puncture position, and an actuator mechanism disposed in the housing for causing the lancet holder to move from the cocked position to the puncture position. The lancet assembly has a lancet with a sharp tip, a lancet body having at least two angularly spaced ribs which extend outwardly from a central portion of the lancet body, and a protective cap covering the sharp tip of the lancet, the protective cap being attached to the lancet body so that the protective cap is twistably removable from the lancet body.

The lancet holder has an aperture formed therein, the aperture having a cylindrical shape and being substantially unobstructed so that the lancet body may be inserted into the aperture in any angular orientation relative to the lancet holder, and the blood sampling device includes means for preventing significant rotational movement of the lancet body relative to the lancet holder when the lancet body is disposed in the aperture formed in the lancet holder and when the protective cap is subject to an angular force sufficient to twist the protective cap off of the lancet body.

The cylindrical aperture formed in the lancet holder may be defined by a plurality of curved interior surfaces, and the preventing means may be provided as a plurality of grooves formed in the lancet holder, each of the grooves separating an adjacent pair of the curved interior surfaces. The blood sampling device may also include means for maintaining the lancet holder in the cocked position and means for releasing the lancet holder from the cocked position to cause the actuator mechanism to force the lancet holder from the cocked position to the puncture position.

These and other features of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENT

Figure 1:
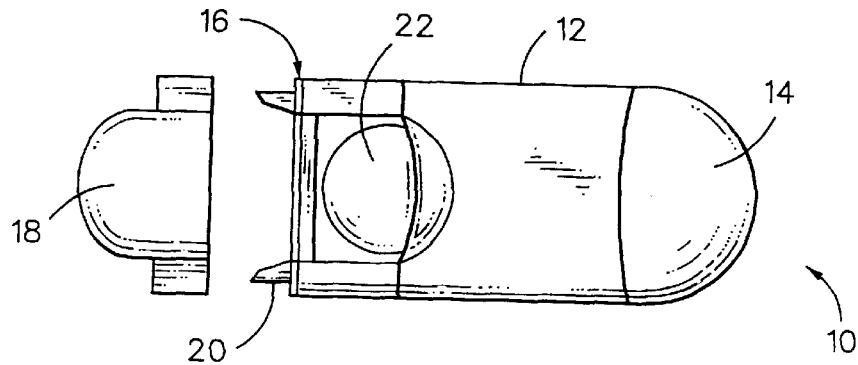
FIG. 1 is a top view of one embodiment of a blood sampling device in accordance with the invention.
Figure 2:
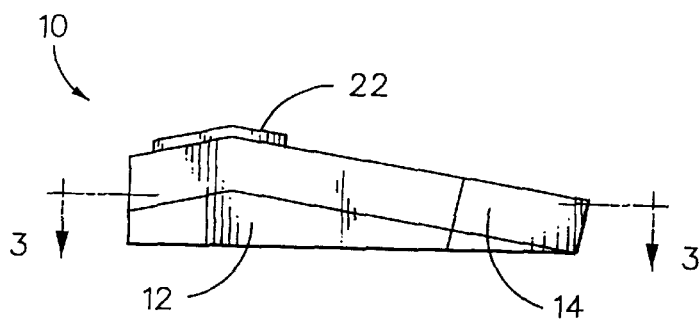
FIG. 2 is a side view of the blood sampling device of FIG. 1.

FIG. 1 illustrates a preferred embodiment of a blood sampling device 10 for taking a sample of blood from a person. Referring to FIG. 1, the blood sampling device 10 has a main housing portion 12, a housing portion 14 movable relative to the main housing 12, an end cap support 16 connected to the main housing 12, and an end cap 18 that may be attached to the end cap support 16 and supported thereon by a pair of support arms 20 integrally formed with the end cap support 18.

When used, the movable housing 14 is pulled away from the main housing 12 to move an internal lancing mechanism to a cocked position, and then a pushbutton 22 is pushed to actuate the lancing mechanism so that the sharp tip of a lancet is forced through a hole (not shown) in the left-hand end of the end cap 18 to cause a skin puncture to be made. The blood sampling device 10 may be provided with a number of different end caps 18, each having a different width, to facilitate the formation of skin punctures of various depths.

Figure 3:
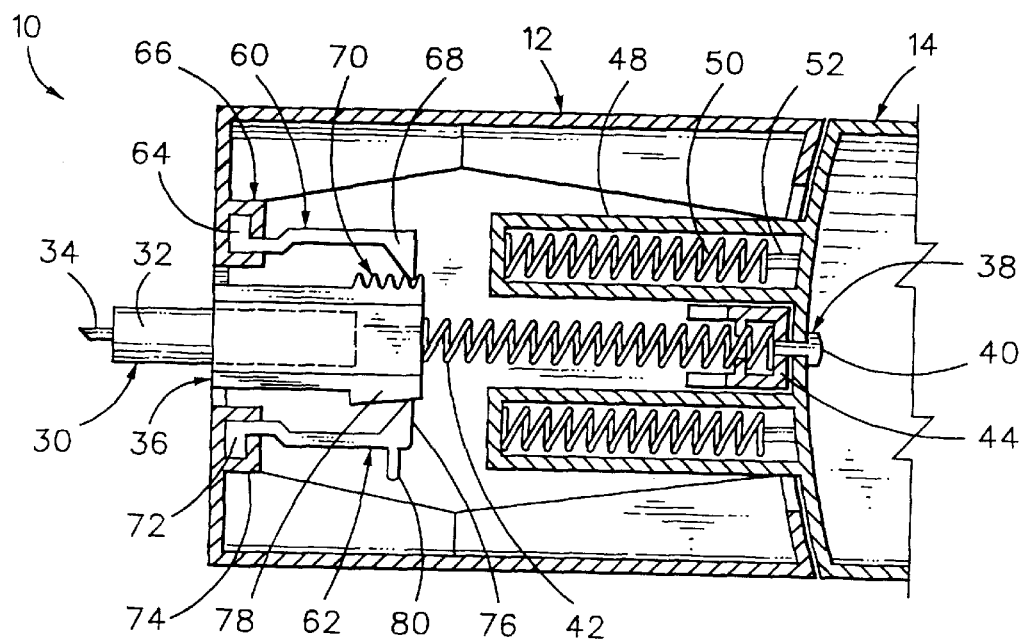
FIG. 3 is a cross-sectional view of a portion of the blood sampling device taken along lines 3—3 of FIG. 2.

FIG. 3 is a cross-sectional view of a portion of the blood sampling device 10 with the end cap 18 and end cap support 16 not shown. Referring to FIG. 3, a lancet assembly 30 having a lancet body 32 (schematically shown) and a lancet 34 is frictionally supported within an internal cylindrical aperture formed in a cup-shaped lancet holder 36 by an interference fit between outer portions of the lancet body 32 and curved inner surfaces in the interior of the lancet holder 36.

The lancet holder 36 is connected to an elongate shaft 38 by being integrally formed therewith. The shaft 38 has an enlarged end 40 which is supported within the movable housing 14. A drive spring 42 is disposed around the shaft 38 between the lancet holder 36 and a C-shaped spring stop 44 (see also FIG. 4) integrally formed with the main housing 12.

The movable housing 14 has a pair of elongate spring trays 48 integrally formed therewith. A return spring 50 is disposed within each of the spring trays 48, the left end of each return spring 50 being disposed against a left-hand internal surface of the spring tray 48 and the right end of each return spring 50 being disposed against a spring stop 52 integrally formed with the main housing 12. The spring stops 52 extend into the spring trays 48 through an elongate slot 54 (see FIG. 4) formed in the bottom portion of each tray 48.

Referring to FIG. 3, a damping arm 60 and a retaining arm 62 are disposed adjacent opposite sides of the lancet holder 36. The damping arm 60 has a first end 64 which is held within a retaining structure 66 integrally formed with the main housing 12 and a second pointed end 68 which is disposed adjacent a corrugated surface 70 formed on an outside portion of the lancet holder 36. The retaining arm 62 has a first end 72 which is held within a retaining structure 74 integrally formed with the main housing 12 and a second pointed end 76 which is disposed adjacent an angled stop member 78. The lower side of the retaining arm 62 rests on a support member 80. The arms 60, 62 are biased inwardly towards the lancet holder 36 so that they make contact with the outer sides of the lancet holder 36.

Figure 4:
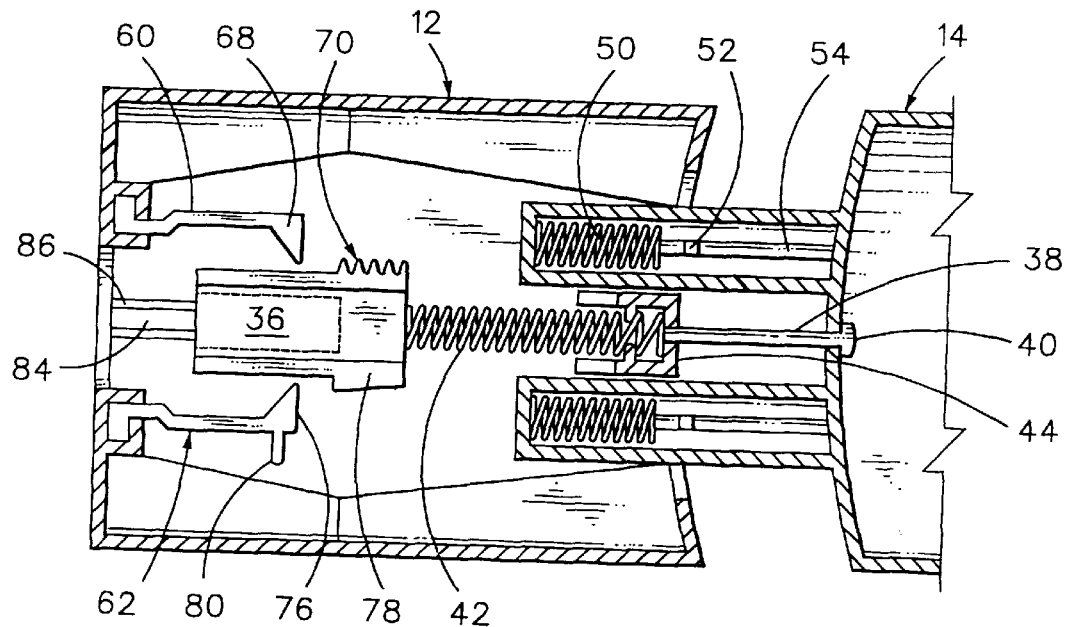
FIG. 4 is a cross-sectional view of the portion of the blood sampling device shown in FIG. 3 when the blood sampling device is in a cocked position.

FIG. 3 shows the interior of the blood sampling device 10 when not in use when the lancet holder 36 is disposed in a resting position between a puncture position and a cocked position. FIG. 4 illustrates the interior of the blood sampling device 10 (the lancet assembly 30 is not shown) when the lancet holder 36 is in a cocked position in which the movable housing 14 has been pulled away from the main housing 12.

Referring to FIG. 4, to move the lancet holder 36 from its resting position to its cocked position, the movable housing 14 is pulled away from the main housing 12, against the force of the drive spring 42, until the angled stop member 78 formed on the lancet holder 36 moves past (to the right of) the pointed end 76 of the retaining arm 62. At that point, the bias of the retaining arm 62 will force its pointed end 76 inwardly, so that the pointed end 76 makes contact with the side of the lancet holder 36 disposed to the left of the angled stop member 78. When in that cocked position, leftward movement of the lancet holder 36 due to the drive spring 42 is prevented due to the contact between the pointed end 76 of the retaining arm 62 and the angled stop member 78. After the lancet holder 36 is placed in the cocked position, the user allows the return springs 50 to force the movable housing 14 back to its initial position adjacent the main housing 12.

The lancet holder 36 is guided between its resting and cocked positions by a guide rib 82 (FIG. 7) formed on the bottom portion of the lancet holder 36 that rides within a groove 84 formed between a pair of raised guide rails 86 formed in a bottom interior portion of the main housing 12.

Figure 5:
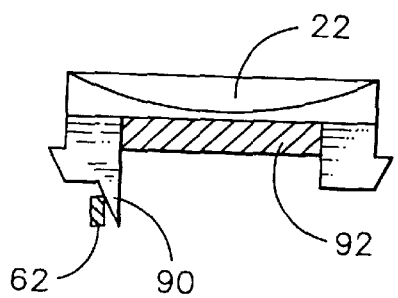
FIG. 5 is a side view of a portion of a release mechanism incorporated within the blood sampling device.

To make a skin puncture, the end cap 18 is attached to the blood sampling device 10 with the lancet holder 36 in the cocked position, the end cap 18 is placed firmly against the skin where the puncture is to be made, and the pushbutton 22 is pressed. Referring to FIGS. 4 and 5, pressing the pushbutton 22 will cause an angled release arm 90 (FIG. 5), integrally formed with the bottom of the pushbutton 22 and which passes through an aperture (not shown) in the main housing 12, to force the retaining arm 62 away from the lancet holder 36 so that leftward movement of the lancet holder 36 is no longer prevented by the contact of the angled stop member 78 with the pointed end 76 of the retaining arm 62. As shown in FIG. 5, spring means in the form of an elastically deformable foam material 92 is disposed between the pushbutton 22 and a portion of the main housing 12 to bias the pushbutton 22 to its non-actuated position.

Upon release of the lancet holder 36 as described above, the drive spring 42 will force the lancet holder 36 to the left in FIG. 4 until the sharp point of the lancet 34 (FIG. 3) passes through the hole (not shown) in the end cap 18 to make the puncture. When the puncture is made, the drive spring 42 will be in a stretched position, and immediately after the puncture is made the contraction of the drive spring 42 will draw the lancet assembly 36 back towards its resting position shown in FIG. 3.

As the lancet holder 36 moves from its puncture position back to its resting position shown in FIG. 3, the pointed tip 68 of the damping arm 60 will make frictional contact with the corrugated surface 70, which frictional contact will decelerate or damp the movement of the lancet holder 36. Such damping prevents the drive spring 42, due to its natural tendency to oscillate (due to its being elastically deformable), from causing a second, unintended skin puncture to be made. As used herein, the term "corrugated" refers to a surface having raised ribs or other structures, either regularly or irregularly spaced, for providing an increased amount of friction when the surface is brought into contact with a damping member.

Figure 7:
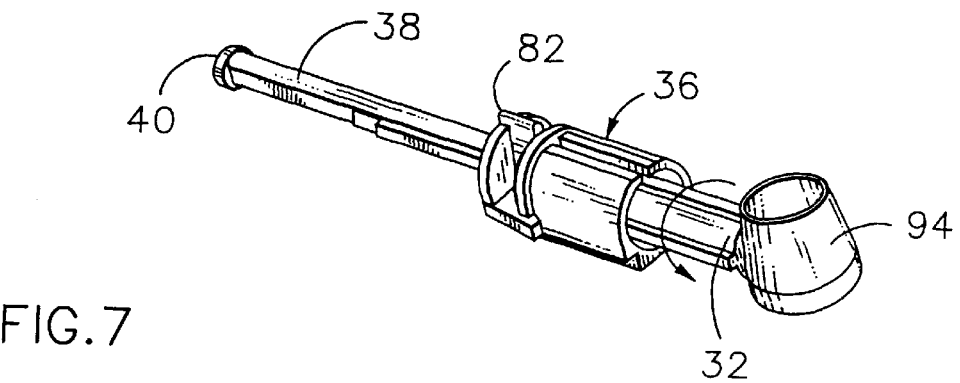
FIG. 7 is a perspective view of the lancet assembly disposed within the lancet holder.

FIG. 7 is a perspective view of the lancet assembly 30 disposed within the lancet holder 36. Referring to FIG. 7, the lancet assembly 30 is shown with a protective cap 94 which has a portion that is integrally formed with the lancet body 32 and which covers the sharp point of the lancet 34. Prior to using the blood sampling device 10, the lancet body 32 of a new lancet assembly 30 is inserted into the cylindrical aperture disposed in the lancet holder 36, and then the protective cap 94 is twisted off of the lancet assembly 30, in the direction of the arrow shown in FIG. 7.

Figure 6:
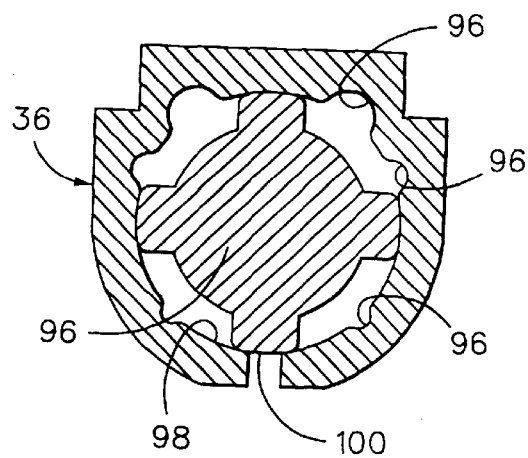
FIG. 6 is a cross-sectional view of a lancet assembly disposed within a lancet holder.

FIG. 6 is an enlarged cross-sectional view of a portion of the lancet body 32 when inserted into the lancet holder 36. Referring to FIG. 6, to prevent significant rotation of the lancet assembly 30 relative to the lancet holder 36 when the protective cap 94 is twisted off, the interior of the lancet holder 36 is provided with six grooves 96, each of the grooves 96 being disposed between an adjacent pair of curved surfaces 98 which together define the cylindrical shape of the internal aperture formed in the lancet holder 36. The edges between the grooves 96 and the curved surfaces 98 act to prevent significant rotation of the lancet body 32 by making contact with four angularly spaced ribs 100 which extend outwardly from a center portion of the lancet body 32.

Because cylindrical aperture formed in the lancet holder 36 is substantially unobstructed by internal ribs or other structures, the lancet body 32 may be inserted into the cylindrical aperture in any angular orientation relative to the lancet holder 36.

All of the components of the blood sampling device 10, except for the springs 42, 50, the lancet 34, and the foam material 92, may be composed of plastic.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A blood sampling device, comprising:
   a housing (12);
   a lancet assembly (36) comprising:
      a lancet having a sharp tip;
      a lancet body (32) which supports said lancet, said lancet body (32) having at least two angularly spaced ribs which extend outwardly from a central portion of said lancet body (32); and
      a protective cap (94) covering said sharp tip of said lancet, said protective cap (94) being attached to said lancet body (32) so that said protective cap (94) is twistably removable from said lancet body;
   a lancet holder (36) which is movable in a lancing direction between a cocked position and a puncture position, said lancet holder having an aperture formed therein, said aperture having a cylindrical shape and being substantially unobstructed so that said lancet body (32) may be inserted into said aperture in any angular orientation relative to said lancet holder (36);
   an actuator mechanism disposed in said housing for causing said lancet holder (36) to move from said cocked position to said puncture position; and
   means for preventing significant rotational movement of said lancet body (32) relative to said lancet holder (36) when said lancet body (32) is disposed in said aperture formed in said lancet holder (36) and when said protective cap (94) is subject to an angular force sufficient to twist said protective cap (94) off of said lancet body (32),
   wherein said aperture is defined by a plurality of curved interior surfaces (98) and wherein said preventing means comprises a plurality of grooves (96) formed in said lancet holder (36), each of said grooves separating an adjacent pair of said curved interior surfaces (98).

2. A blood sampling device as defined in claim 1 wherein said aperture is defined by at least four curved interior surfaces and wherein said preventing means comprises four grooves formed in said lancet holder, each of said grooves separating an adjacent pair of said curved interior surfaces.

3. A blood sampling device as defined in claim 1 wherein said aperture is defined by at least six curved interior surfaces and wherein said preventing means comprises six grooves formed in said lancet holder, each of said grooves separating an adjacent pair of said curved interior surfaces.

4. A blood sampling device as defined in claim 1 additionally comprising:
   means for maintaining said lancet holder in said cocked position; and
   means for releasing said lancet holder from said cocked position to cause said actuator mechanism to force said lancet holder from said cocked position to said puncture position.

5. A blood sampling device, comprising:
   a housing (12);
   a lancet assembly (30) comprising:
      a lancet having a sharp tip;
      a lancet body (32) which supports said lancet, said lancet body (32) having at least two angularly spaced ribs which extend outwardly from a central portion of said lancet body (32); and
      a protective cap (94) covering said sharp tip of said lancet, said protective cap (94) being attached to said lancet body (32) so that said protective cap (94) is twistably removable from said lancet body (32);
   a lancet holder (36) which is movable in a lancing direction between a cocked position and a puncture position, said lancet holder (36) having an aperture formed therein, said aperture having a cylindrical shape and being substantially unobstructed so that said lancet body (32) may be inserted into said aperture in any angular orientation relative to said lancet holder (36);
   a drive spring (42) for forcing said lancet holder (36) from said cocked position to said puncture position;
   means for maintaining said lancet holder (36) in said cocked position;
   means for releasing said lancet holder (36) from said cocked position to cause said drive spring (42) to force said lancet holder (36) from said cocked position to said puncture position; and
   means for preventing significant rotational movement of said lancet body (32) relative to said lancet holder (36) when said lancet body (32) is disposed in said aperture formed in said lancet holder (36) and when said protective cap (94) is subject to an angular force sufficient to twist said protective cap (94) off of said lancet body (32),
   wherein said aperture is defined by a plurality of curved interior surfaces (98) and wherein said preventing means comprises a plurality of grooves formed in said lancet holder (36), each of said grooves separating an adjacent pair of said curved interior surfaces (98).

6. A blood sampling device as defined in claim 5 wherein said aperture is defined by at least four curved interior surfaces and wherein said preventing means comprises four grooves formed in said lancet holder, each of said grooves separating an adjacent pair of said curved interior surfaces.

7. A blood sampling device as defined in claim 5 wherein said aperture is defined by at least six curved interior surfaces and wherein said preventing means comprises six grooves formed in said lancet holder, each of said grooves separating an adjacent pair of said curved interior surfaces.

8. A blood sampling device, comprising:
   a housing;
   a lancet assembly comprising:
      a lancet having a sharp tip;
      a lancet body which supports said lancet, said lancet body having at least two angularly spaced ribs which extend outwardly from a central portion of said lancet body; and
      a protective cap covering said sharp tip of said lancet, said protective cap being attached to said lancet body so that said protective cap is twistably removable from said lancet body;

a lancet holder which is movable in a lancing direction between a cocked position and a puncture position, said lancet holder having an aperture formed therein, said aperture having a cylindrical shape and being substantially unobstructed so that said lancet body may be inserted into said aperture in any angular orientation relative to said lancet holder, said aperture being defined by a plurality of curved interior surfaces and said lancet holder having a plurality of grooves formed therein, each of said grooves separating an adjacent pair of said curved interior surfaces, said curved interior surfaces and said grooves being adapted to prevent significant rotational movement of said lancet body relative to said lancet holder when said lancet body is disposed in said aperture and when said protective cap is subject to an angular force sufficient to twist said protective cap off of said lancet body; and an actuator mechanism disposed in said housing for causing said lancet holder to move from said cocked position to said puncture position.

9. A blood sampling device as defined in claim 8 wherein said aperture is defined by at least four curved interior surfaces and wherein four grooves are formed in said lancet holder, each of said grooves separating an adjacent pair of said curved interior surfaces.

10. A blood sampling device as defined in claim 8 wherein said aperture is defined by at least six curved interior surfaces and wherein six grooves are formed in said lancet holder, each of said grooves separating an adjacent pair of said curved interior surfaces.

11. A blood sampling device as defined in claim 8 wherein said actuator mechanism comprises a drive spring for forcing said lancet holder from said cocked position to said puncture position.

12. A blood sampling device as defined in claim 8 additionally comprising:

means for maintaining said lancet holder in said cocked position; and means for releasing said lancet holder from said cocked position to cause said actuator mechanism to force said lancet holder from said cocked position to said puncture position.

13. A blood sampling device as defined in claim 8 wherein said actuator mechanism comprises a drive spring for forcing said lancet holder from said cocked position to said puncture position and wherein said blood sampling device additionally comprises:

means for maintaining said lancet holder in said cocked position; and means for releasing said lancet holder from said cocked position to cause said drive spring to force said lancet holder from said cocked position to said puncture position.

* * * * *